(12) United States Patent
Foster et al.

(10) Patent No.: US 7,862,751 B2
(45) Date of Patent: Jan. 4, 2011

(54) FORMULATION OF FINE PARTICLES USING LIQUEFIELD OR DENSE GASES

(75) Inventors: Neil Russell Foster, Cherrybrook (AU); Hubert Leonardus Regtop, Mittagong (AU); Fariba Dehghani, Rosebery (AU); Andrian Tandya, New South Wales (AU)

(73) Assignee: MAP Pharmaceuticals, Inc., Mountain View, CA (US)

( * ) Notice: Subject to any disclaimer, the term of this patent is extended or adjusted under 35 U.S.C. 154(b) by 966 days.

(21) Appl. No.: 10/511,245

(22) PCT Filed: Apr. 15, 2003

(86) PCT No.: PCT/AU03/00453

§ 371 (c)(1),
(2), (4) Date: Jul. 26, 2005

(87) PCT Pub. No.: WO03/088951

PCT Pub. Date: Oct. 30, 2003

(65) Prior Publication Data

US 2006/0151900 A1 Jul. 13, 2006

(30) Foreign Application Priority Data

Apr. 15, 2002 (AU) ............................... PS 1744
Mar. 12, 2003 (AU) ............................... 2003901180

(51) Int. Cl.
*B29B 9/00* (2006.01)
(52) U.S. Cl. .......................................... 264/5; 424/489
(58) Field of Classification Search .................. 264/50, 264/5–13
See application file for complete search history.

(56) References Cited

U.S. PATENT DOCUMENTS 6,056,791 A * 5/2000 Weidner et al. ........... 23/295 R (Continued)

FOREIGN PATENT DOCUMENTS

WO WO 97/14407 A1 * 4/1997

(Continued)

OTHER PUBLICATIONS

Kerč et al., "Micronization of drugs using supercritical carbon dioxide," International Journal of Pharmaceutics, 182 (1999), pp. 33-39.*

(Continued)

*Primary Examiner*—Jennifer K Michener
*Assistant Examiner*—Magali P Slawski
(74) *Attorney, Agent, or Firm*—DLA Piper LLP (US)

(57) ABSTRACT

The invention provides a method for manipulating or formulating a solid substance which melts under pressure of a gas without degrading at a temperature lower than the melting point of the substance at atmospheric pressure including: applying to the substance a liquefied gas or dense gas to melt the substance without degrading the substance; then contacting the molten substance with a carrier fluid, which is at substantially the same pressure as the liquefied gas or dense gas, to form a solution or mixture of at least a part of the molten substance and the carrier fluid; and passing the solution or mixture into a vessel of lower pressure than the pressure of the liquefied gas or dense gas and carrier fluid to form particles of the substance; and particles formed by the method.

19 Claims, 12 Drawing Sheets

U.S. PATENT DOCUMENTS 6,316,030 B1 * 11/2001 Kropf et al. .................. 424/489
2002/0110526 A1 * 8/2002 Zhu et al. ..................... 424/46

FOREIGN PATENT DOCUMENTS

| WO | WO 98/15348 | 4/1998 |
| WO | WO99/52504 | 10/1999 |
| WO | WO00/30612 | 6/2000 |

OTHER PUBLICATIONS

Jung, Jennifer and Michel Perrut. "Particle design using supercritical fluids: Literature and patent survey." Journal of Supercritical Fluids 20 (2001) 179-219.*

Thiering et al., The influence of operating conditions on the dense gas precipitation of model proteins, *J. of Chemical Technology and Biotechnology* vol. 75(1), pp. 29-41, 2000.

* cited by examiner

FORMULATION OF FINE PARTICLES USING LIQUEFIELD OR DENSE GASES

CROSS REFERENCE TO RELATED APPLICATIONS

This application is a 371 national stage of International Application No. PCT/AU03/00453 and claims the benefit of priority under 35 USC §119(a)-(d) of International Application No. PCT/AU03/00453, with an international filing date of 15 Apr. 2003, which claims priority to Australian Application No. PS 1744, filed 15 Apr. 2002, and Australian Patent Application No. 2003901180, which are incorporated herein by reference in their entirety.

FIELD

The present invention relates to methods for the formulation of fine particles of products using liquefied gases or dense gases. It has particular but not exclusive application to the precipitation and encapsulation of fine particles from the molten form of the product.

BACKGROUND

Particulate products are of great interest for pharmaceutical applications, where there is a need to obtain particles of reproducible, preferably small, size and shape within a narrow size range. These physical criteria are important because the bioavailability of some pharmaceuticals is dependant on the size of the particles. Similarly, bioavailability may be adjusted by coatings (ie, encapsulation) or dispersion (eg, in a polymer matrix, particularly biodegradable polymers).

There are a number of dense gas techniques which have been used in the micronisation of particles. The two techniques particularly relevant to the present invention are Rapid Expansion of Supercritical Solutions (RESS) and Particles from Gas Saturated Solutions (PGSS).

The RESS process involves the material of interest being dissolved in a supercritical fluid solvent under pressure, and precipitating the solute by depressurising the solution across a nozzle.

The PGSS process involves applying a dense gas under pressure to a molten material. The dense gas dissolves in the material of interest to form a solute saturated solution, and the resulting liquid phase is sprayed through a nozzle into a vessel of lower pressure, which results in the dense gas being vaporised, leaving behind fine particles of the desired material. A typical apparatus for this process is illustrated schematically in FIG. 1 and described in more detail below. The PGSS process is discussed by Kerč et al in *International Journal of Pharmaceuticals*, Vol 182, 1999, 33-39. Since the PGSS process involves first heating the material of interest to its melting point, it is therefore limited to materials which do not thermally degrade below their melting point (ie are not thermally labile). However, as some materials experience a melting point depression in the presence of a dense gas, they may be used in the PGSS process if the dense gas depresses their melting point below the thermal degradation point. Of course, with some substances, these temperature points are not precise especially where the substance exists in different morphologies. Thus, the PGSS process has been found to have limited applications.

Another disadvantage of the PGSS process is that the viscosity of the solution being sprayed, while less than the viscosity of the molten solute, is still at a level that can cause the nozzle to block.

One known formulation method (which may be used, for example, for delayed release formulations) is to spray a molten pharmaceutical (or material of interest) into a solution of a sustained release compound (such as stearate) at increased temperature and pressure. This results in the newly formed particles of the pharmaceutical being coated in the stearate (or other similar compound) for delayed release or other applications. The utility of this method for pharmaceutical applications is restricted to the few pharmaceutical substances known to melt without decomposing.

Co-formulation of pharmaceuticals has also been proposed for increased efficacy or new applications. These may however be difficult to prepare, particularly if melting a compound so as to mix it with another partly decomposes it.

In attempting to overcome some of those difficulties and limitations, it has surprisingly been found that some compounds exhibit a melting point depression when exposed to a dense gas, which permits use of a dense gas process with such compounds. This process can be used with substances otherwise considered unsuitable given their melting point under normal conditions.

SUMMARY OF THE INVENTION

This invention is directed to substances whose melting point is depressed in the presence of a liquefied gas or a dense gas.

In one embodiment of the invention, there is provided a method for manipulating or formulating a substance which melts under pressure of a gas without degrading at a temperature lower than the melting point of the substance at atmospheric pressure including:

applying to the substance a liquefied gas or dense gas to melt the substance without degrading the substance;

then contacting the molten substance with a carrier fluid, which is at substantially the same pressure as the liquefied gas or dense gas, to form a solution or mixture of at least a part of the molten substance and the carrier fluid; and passing the solution or mixture into a vessel of lower pressure than the pressure of the liquefied gas or dense gas and carrier fluid to form particles of the substance.

Preferably, the substance is a pharmaceutical or biological compound. Examples include cyclosporine and ibuprofen. Usually the substance will be solid at atmospheric pressure and temperature.

Preferably, the contacting step is conducted at relatively constant temperature and pressure.

Preferably, the temperature is between 5° C. and 150° C., and the pressure of the liquefied gas or dense gas and carrier gas is between 5 bar and 200 bar.

Preferably, the liquefied gas or dense gas is $CO_2$.

The term biological compound as used throughout this specification refers to any natural or synthetic substance which possesses a biological activity such as, for example, an enzymatic activity, channel function (e.g. ion channel), receptor or binding function, hormonal or neurotransmitter activity, or other pharmacological activity, or a protein, polypeptide, peptide, peptide analog or peptidomimetic, or nucleic acid or nucleic acid in association with a protein, polypeptide or peptide.

The biological compound is preferably selected from the group consisting of an antimicrobial agent, virus, antiviral agent, antifungal pharmaceutical, antibiotic, nucleotide, DNA, antisense DNA, RNA, antisense RNA, amino acid, peptide, protein, enzyme, hormones, immune suppressant, protease inhibitors, thrombolytic anticoagulant, central nervous system stimulant, decongestant, diuretic vasofilator, antipsychotic, neurotransmitter, sedative, anaesthetic, surfactant, analgesic, anticancer agent, anti-inflammatory, antioxidant, antihistamine, vitamin, mineral, sterol, phytosterol, lipid and esters of fatty acids.

In terms of terminology used, "PGSS" is often used as a shorthand reference to a process whereby a solid is melted by pressure from a dense gas. The melt can then be sprayed, for example, to form fine particles of the solid upon depressurisation. In our patent application no PS1744, we referred to the process of the invention as a "PGSS" process. However, PGSS is a broader term potentially encompassing processes in addition to the process of the invention. Accordingly, in our patent application number AU 2003901180 and in this specification, we use the acronym "PDGIMS" (Particles from Dense Gas Induced Molten Solutions) to refer to the same general process of the invention. The key determinants of a process are the steps, conditions and reagents.

The invention can also be used to encapsulate a material, such as a pharmaceutical substance. In one particular application, where it is desirable to release one drug before another into a metabolic system, the latter drug may be coated with or co-precipitated with the former by means of this process. This would be particularly suitable if, for example, the first drug aided absorption or inhibited premature degradation/metabolism of the second, which was the primarily active drug. One proposed example of this application of the invention is paclitaxel coated with cyclosporine. Combinations of immunosuppressives are also contemplated. Accordingly, in one application of the invention, paclitaxel is coated with molten cyclosporine at temperatures only moderately above atmospheric.

In another embodiment, the method described above can be used to produce micronised particles of the substance encapsulated by another material, such as a polymer, preferably a biodegradable polymer. This polymer coating can be selected to impart various properties to the particles, for example, to enable delayed release of the encapsulated material.

Alternatively, the micronised particles may contain a mixture or combination of the substance and a relatively, biologically inert material for sustained release applications. In a further embodiment, pharmaceutical or biological compounds may be co-precipitated to form micronised particles enabling coadministration (ie simultaneous bioavailability of the substances.

Preferably, the encapsulating material is selected from the group consisting of polyethylene glycol, polyvinylpyrrolidone, poly(d,l-lactide-co-glycolide), poly cellulose acetate.

For example, the molten substance under the liquefied gas or dense gas could be depressurised through a nozzle so as to precipitate fine particles of the substance. These can then be coated with known coatings (eg, stearate, polylactides, polyethylene glycol, polyvinylpyrrolidone, poly(d,l-lactide-co-glycolide), or poly cellulose acetate) to formulate the substance for medical administration. The invention can also enable a compound, particularly a lipophillic compound, to be embedded into a lecithin vesicle by depressurising into an aqueous solution to produce an emulsion.

In another embodiment of the invention, there is provided particles of a substance formed by the method as described above.

Preferably, the particles include a pharmaceutical or biological compound.

Preferably, the particles include primarily cyclosporine.

Preferably, at least 50% of the particles are between 50 and 5000 nanometers in diameter.

The invention has particular advantage where the substance undergoes degradation or decomposition at temperatures between its lowered melting point and up to about its melting point at atmospheric pressure. This is because the substance can be melted with reduced degradation or decomposition.

In another embodiment of the invention there is provided a method of treatment of a subject including administering to the subject an effective amount of fine particles of a substance produced by the method as described above.

In another embodiment of the invention there is provided a pharmaceutical composition including particles of a substance produced by a method as described above.

The pharmaceutical composition is preferably in a form suitable for inhalation delivery, for example, for delivery by a metered dose inhaler or a nebuliser. Further, a transdermal delivery system may be used (eg, recent devices involving laser-generated or high-pressure dermal channels) and more traditional parenteral administration.

In another embodiment of the invention, there is provided an apparatus for producing particles by the method as described above, including:

a pressure chamber having an inlet and an outlet, the outlet being above the inlet;

a first conduit means connected to the inlet for supplying the liquefied gas or dense gas to the pressure chamber; and a second conduit means extending from the outlet to a depressurisation point.

Preferably, the apparatus further includes flow control means to control flow along the second conduit means.

Preferably, the apparatus further includes a third conduit means connected to the downstream end of the second conduit means downstream of the flow control means for supplying liquefied gas or dense gas, or carrier fluid, at pressure to the depressurisation point. The flow of fluid through the conduit means will generally be controlled by valves.

Preferably, the depressurisation point is a nozzle.

In use of the apparatus according to the invention, the first conduit means connects a source of the liquefied gas or dense gas to the inlet, such as a gas bottle. The substance is preloaded into the pressure chamber adjacent the inlet. The gas is then permitted to enter the pressure chamber through the inlet and pressurise the chamber as the second and third conduit means are closed.

The temperature of the system and pressure of the chamber are selected and then monitored during the process such that the substance melts at its depressed melting point and then is left to equilibrate. Having formed a homogenous solution of substance/gas, the system is pressurised by opening the third conduit means. Gas can thus flow from its source, past the inlet to the depressurisation point to pressurise the system. Once pressurised, the second conduit means is opened, and the third conduit means partly or wholly closed, so as to force the solution from the pressure chamber, through the outlet, along the second conduit means to the depressurisation point/nozzle, where the solution expands to precipitate fine particles.

Flow rates are adjusted, as appreciated by one skilled in the art, to optimise the particle formation.

In another embodiment of the invention, the solution is formed continuously so that the PDGIMS process is continuous rather than batch.

In addition, the invention may be used to facilitate administration of pharmaceuticals which are themselves difficult to administer, such as pharmaceuticals having low blood solubility. In place of known techniques whereby micro-emulsions of such pharmaceuticals may be formulated for administration to patients, the invention can be used to coat nano-sized particles of the active ingredient in a compound which facilitates blood solubility and is, itself, biodegradable.

The invention may also be used to formulate micron-sized or nano-sized particles of thermally labile compounds as these can be manufactured using the invention well below the decomposition temperature of the pharmaceutically active substance itself yet still be formed into very small particles. The invention also avoids the polymorphism of crystal structure which often results from known methods (eg, crystallising particles from ethanol). Polymorphism can significantly change the bioavailability of a substance, which in turn may require new regulatory approval. Thus, the ability to formulate a substance by melting it at significantly lower temperatures is significant to avoid decomposition, and the rapid formation of the particles (with greater control over the system compared with known techniques) reducing the likelihood of polymorphic forms of the substance being generated.

Advantages of the present method include:

(i) the liquefied gas or dense gas saturated with solute used in PDGIMS is less viscous than the solution used in the PGSS process. PDGIMS therefore allows more convenient processing.

(ii) the method can be used for substances that are not suitable for PGSS (eg, PGSS cannot be used for substances that do not have sufficiently low viscosity when molten to be sprayed).

(iii) the method can be conducted without the presence of organic solvents;

(iv) since the materials melt at a lower temperature than normal, the method is suitable for thermally labile compounds and core or coated compounds;

(v) the method is more energy efficient than at least some other dense gas processes, because lower temperatures and/or pressures are used;

(vi) less liquefied gas or dense gas is needed than at least some other dense gas processes, which saves costs.

Without being bound by any particular theory or mode of action, it appears that this melting point depression is caused by the absorption of the liquefied gas or dense gas into the solid matrix and the resulting solute-solvent intermolecular interactions. The liquefied gas or dense gas therefore effectively dissolves in the liquefied substance (eg, cyclosporine).

In this specification, the term "dense gas" is used to refer generally to a fluid substantially near or above its critical pressure (Pc) and temperature (Tc). For practical purposes, the pressure of the fluid is usually in the range (0.9-1.2)Pc and its temperature (0.9-1.2)Tc, but these are examples of typical ranges, not limiting examples. The terms "dense gas", "dense fluid" and "expanded fluid" are used synonymously in this specification.

The term "liquefied gas" is used in contradistinction to "dense gas" or "expanded fluid" to mean a subcritical gas in the liquid phase as a result of elevated pressure at a given temperature.

It will be understood that the term "comprises" (or its grammatical variants) as used in this specification is equivalent to the term "includes" and should not be taken as excluding the presence of other elements of features.

Examples of the invention will now be described for greater clarity of the description of the invention. The examples do not limit the scope of the invention described.

EXAMPLE 1

Cyclosporine is an immunosuppressant used, for example, to prevent organ rejection in transplant patients, and has a melting point of 148-197° C., depending on its crystalline structure. Cyclosporine A, for example, which is a crystalline form, has a melting point of 148-151°. This melting point can be depressed by liquefied carbon dioxide, or dense gas carbon dioxide at pressure. For example, when exposed to carbon dioxide at 65 bar pressure (6.5 Mpa) Cyclosporine A melts at 45° C.

Figure 3:
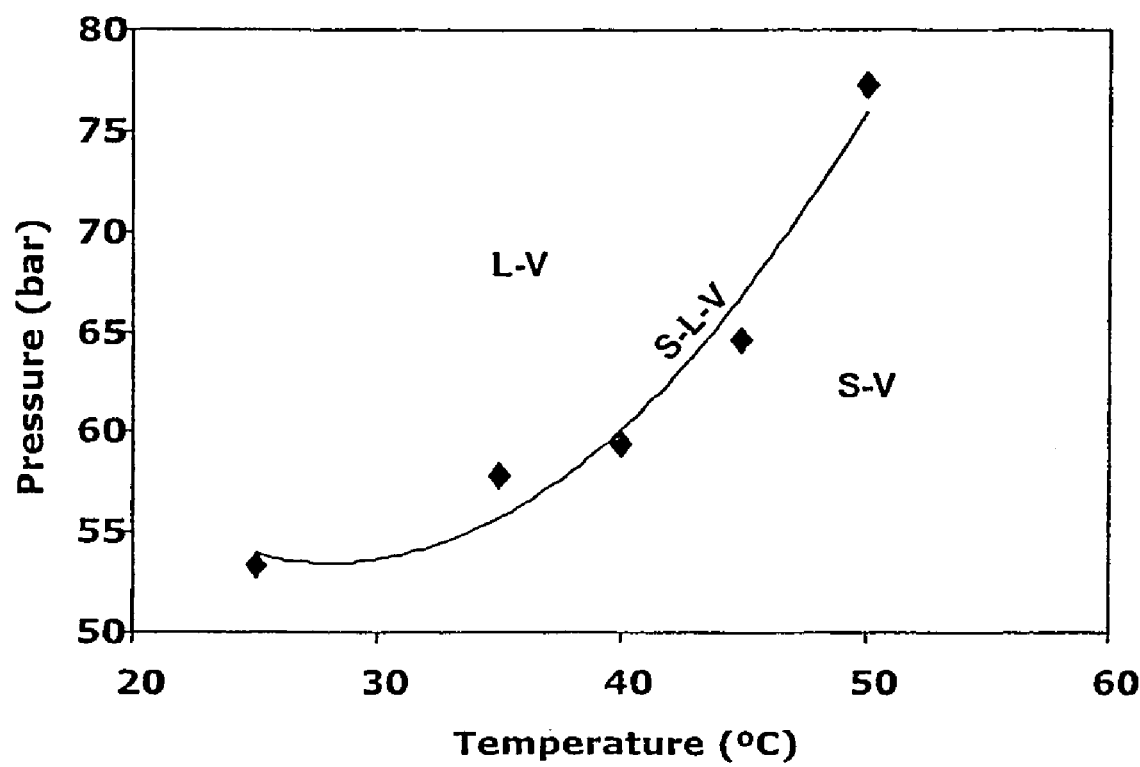
FIG. 3 shows a pressure-temperature diagram for the cyclosporine-$CO_2$ system.
Figure 4:
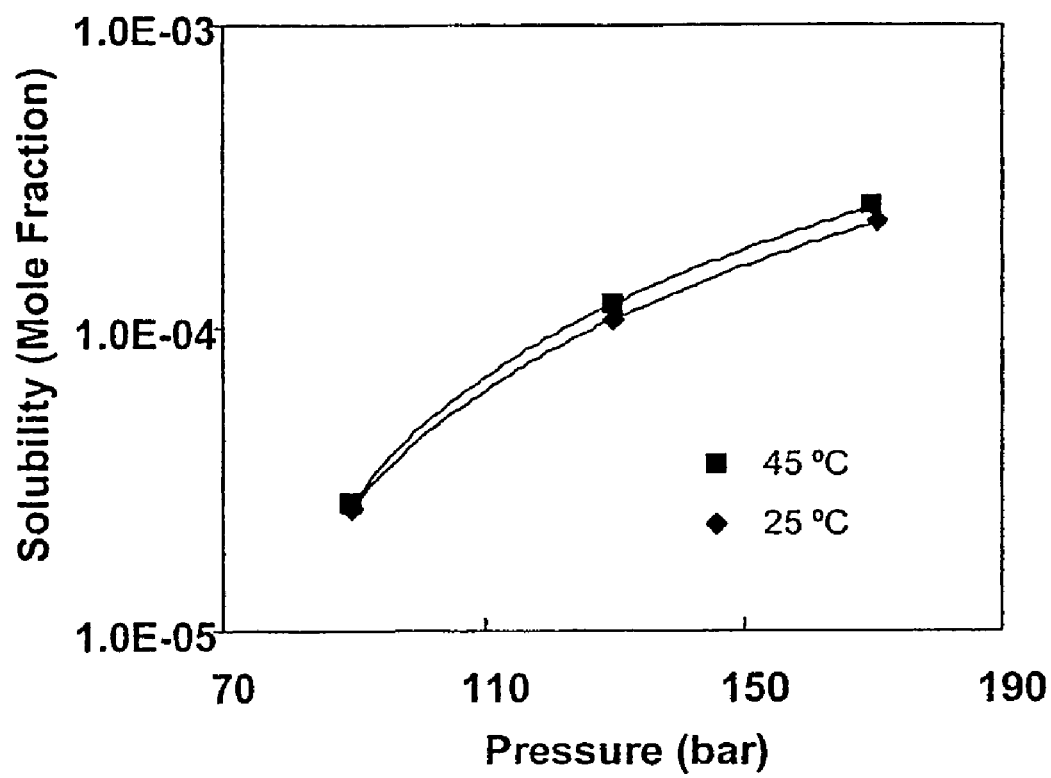
FIG. 4 is a diagram showing the solubility of cyclosporine at various pressures.

A phase behaviour study was conducted to determine the optimum conditions for the melting point depression, the solubilisation of cyclosporine in $CO_2$, and for the particle formation. FIG. 3 shows the melting point depression of cyclosporine at various pressures by a pressure-temperature diagram for the cyclosporine-$CO_2$ system. FIG. 4 shows the solubility of cyclosporine at various pressures. The solubility of cyclosporine in liquefied or dense gas $CO_2$ is high, and its solubility increased as the pressure of the system was changed from 100 to 180 bar.

The phase observation study of the solute-$CO_2$ system was carried out using a static technique. A glass tube (i.d.=5.8 mm) loaded with the solute cyclosporine was placed inside the view cell (Jerguson sight gauge series No. 32). The system was then immersed in the constant temperature water bath. Prior to commencing experiments, the system was purged with low pressure $CO_2$ in order to remove moisture and air. Carbon dioxide was gradually fed into the view cell at 3 bar increments. The system was isolated and equilibrated for at least 10 minutes after each increase in pressure in order to observe any phase transition of the solute.

The melting point of cyclosporine was depressed when contacted with $CO_2$ at 45° C. and 65 bar. The normal melting point of cyclosporine is a function of its crystal structure and varies between 148° C. and 197° C. The pressure temperature diagram for the cyclosporine-$CO_2$ system is presented in FIG. 3. As the data in FIG. 3 shows, upon increasing the $CO_2$ pressure, the temperature at which cyclosporine melted increased, but the melting point was still well below the usual melting point.

The parameters of the melting point depression observed for cyclosporine were then analysed as follows. The melting point of the drug decreased from about 148° C. to 25° C., 35° C., 40° C. and 50° C. when pressurised with $CO_2$ at 53, 58, 60 and 77 bar, respectively. Micronisation of the cyclosporine by PDGIMS is thus efficient due to the significant drop in melting point at relatively moderate pressures.

The solubility of cyclosporine in liquefied or dense gas $CO_2$ was high. The solubility of cyclosporine increased as the pressure of the system was changed from 100 to 180 bar (FIG. 4). The degree of solubility was slightly increased when the temperature increased from subcritical (25° C.) to supercritical (45° C.) conditions. Thus, it can be seen that, due to the considerable solubility of cyclosporine in $CO_2$ and melting point depression behaviour, PDGIMS is an efficient method for micronisation.

EXAMPLE 2

Figure 1:
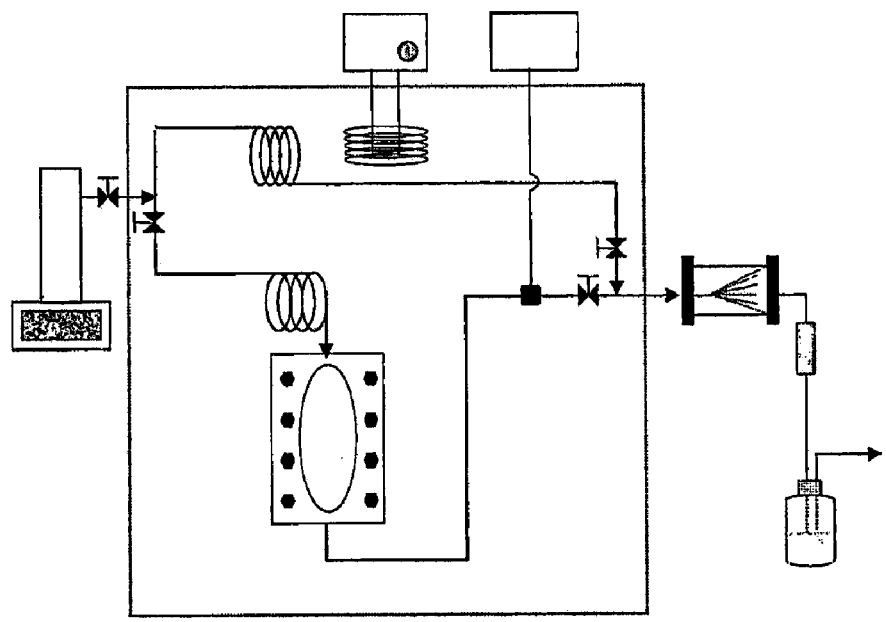
FIG. 1 shows schematically the apparatus used to perform PGSS.
Figure 2:
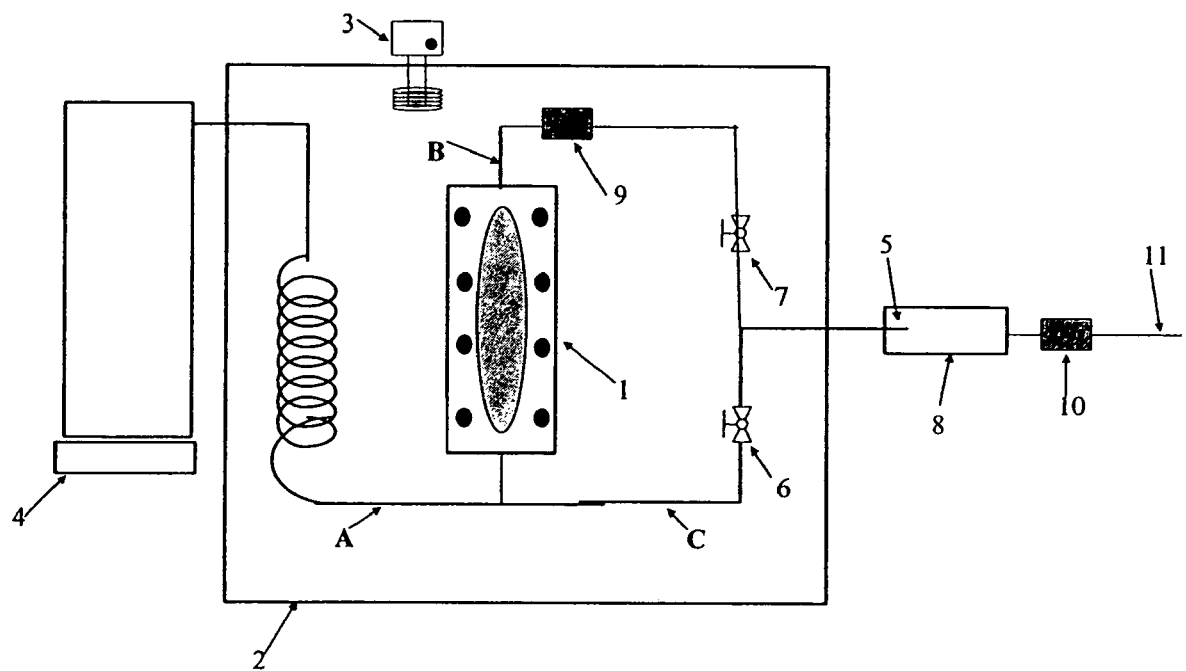
FIG. 2 shows schematically the apparatus used to perform the method of the present invention (PDGIMS).

A schematic diagram of the PDGIMS rig used in the method of this invention is shown in FIG. 2. Cyclosporine is packed into the Jerguson view cell, 1, being a pressure chamber, with glass wool. The purpose of the glass wool is to ensure that the molten cyclosporine remains in the view cell, 1. The carbon dioxide can be in supercritical state, a near critical state, or in a liquid state (eg 25° C. and 60 bar). The cell is then placed in the water bath, 2, heated by the thermostat heater, 3, to keep the temperature constant at 25° C. Carbon dioxide is introduced into the system via line A, to the bottom of the view cell, 1. The pressure in the system is controlled by a high pressure syringe pump, 4. As the carbon dioxide pressure increases, the cyclosporine eventually melts (as can be seen from FIG. 3, at 25° C., the minimum pressure required to melt cyclosporine is 53 bar. and at pressures above this value, the cyclosporine will be molten). The molten cyclosporine was left isolated in the water bath, 2; for at least two hours to equilibrate before further processing. It may be, however, that the equilibration does not require 2 hours. Line C is a bypass line, which is used to pressurise the nozzle, 5, and for cleaning the nozzle at the end of a run. After Line C and the nozzle have been brought to the operating pressure (the nozzle itself providing sufficient resistance to enable pressurisation), the ball valve, 6 on Line C is used to pressurise the nozzle, 5 (thus avoiding a pressure drop and particle formation before the nozzle, which can cause the nozzle to block.) After the nozzle, 5 is pressurised, the ball valve (7) on Line B is opened, allowing a flow of carbon dioxide through the molten cyclosporine. The gas/cyclosporine mixture is then sprayed into the expansion chamber, 8 (via filter, 9), where particles are formed. A filter, 10 is used to trap all particles within the expansion chamber, 8, and the carbon dioxide is vented from the system through outlet, 11. At the end of the run, ball valve, 7 on line B is closed, and ball valve, 6 on line C is opened, allowing a flow of carbon dioxide through the nozzle, clearing any blockages or material remaining in the system.

One way in which this configuration differs from the configuration of typical PGSS rigs is that the liquefied gas or dense gas is forced from the bottom of the Jerguson view cell to the top. In most PGSS rigs, the gas is fed from the top of the view cell. The purpose of this change in the configuration, is to deliberately keep the liquefied gas or dense gas solution below saturation. This assists in avoiding blockages in the 50 micron nozzle.

The unprocessed cyclosporine contained large irregular crystals with particles in the range of 100 μm (FIG. 5(a)). The primary particles produced by the PDGIMS process at 25° C. and 160 bar were spherical, and on average 100 to 200 nm in diameter (FIG. 5(b)). Other examples of particles produced by the PDGIMS process are shown in FIG. 6 (45° C., 200 bar and 50 μm nozzle) and FIG. 7 (25° C. and 170 bar). The particles shown in FIGS. 6 and 7 are also on average 100 to 200 nm in diameter.

Cyclosporine produced by this technique showed a significant loss of crystallinity, as discussed further below.

EXAMPLE 3

The following conditions were maintained during the process:
post-expansion pressure: maintained below 3 bar with a pressure relief valve;
post expansion temperature: room temperature;
particle collection device: particles are collected in a perspex expansion chamber, or a Whitey Chamber. No change in particle morphology or size was observed with the change in particle collection device. The carbon dioxide, in a gas form, leaves the particle collection device via an outlet line. Between the particle collection device and the outlet line is a 0.5 μm filter, which will let particles smaller than 0.5 μm past. Significant amounts of powder were seen in the outlet line after the filter, which was one measure of the size of the particles formed. These particles must be smaller than 0.5 μm to be able to pass the filter.

In the method of the invention, the following parameters can be varied:
pre-expansion pressure: between 60 and 200 bar—the solubility of cyclosporine increases as the pressure increases;
pre-expansion temperature: 25° C., 40° C. and 45° C.—no change in particle morphology or solubility of cyclosporine in carbon dioxide is observed with the change of temperature;

Further, again without wishing to be bound by any specific modality of operation, it is believed that the porous structure that was observed in the microspheres might be caused by diffusion of carbon dioxide from the microspheres during the expansion stage.

As shown in FIG. 6, the particle size of cyclosporine was not significantly influenced by the pressure and temperature of the system (cf FIG. 5(b)—particles produced at 25° C. and 160 bar). However, the PDGIMS process was more efficient (ie, a greater yield of product) at high pressures, such as 200 bar, and temperatures such as 45° C.

Figure 8:
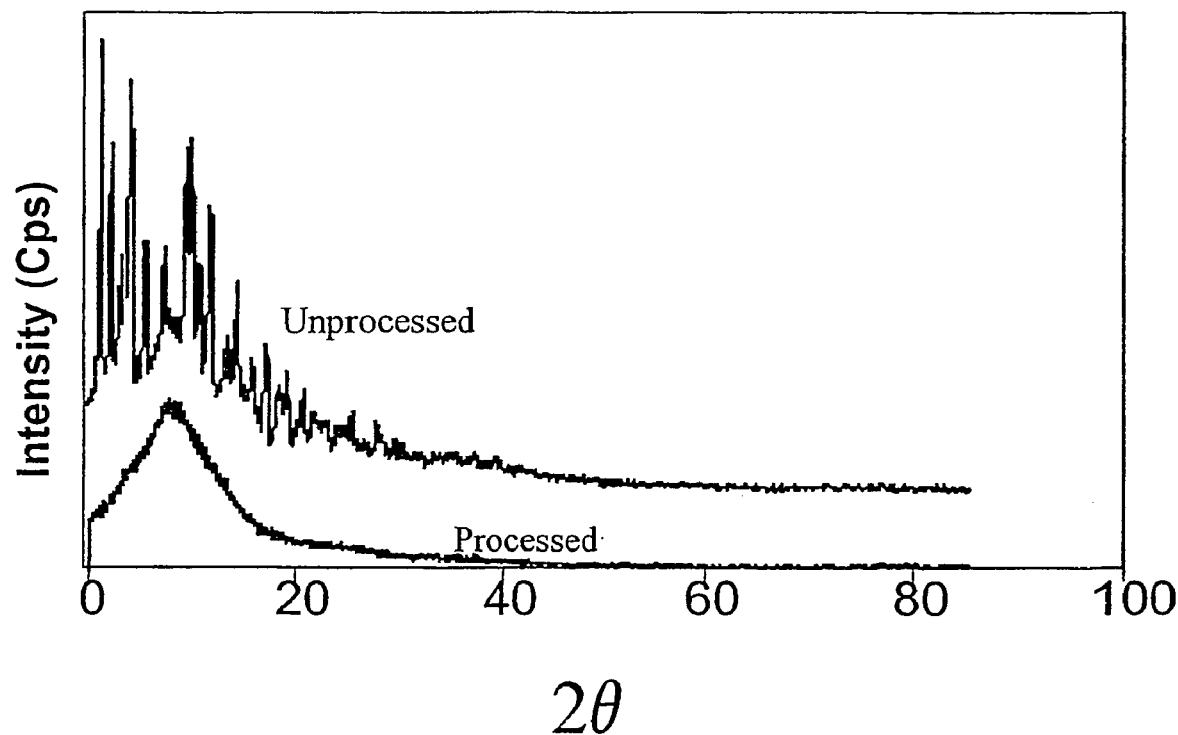
FIG. 8 shows X-ray diffraction (XRD) analysis for cyclosporine.

The degree of crystallinity and polymorphic form of the cyclosporine was examined by x-ray diffraction (XRD). The results obtained from XRD analysis shown in FIG. 8 indicate that the original powder was in crystalline form. The XRD analysis confirmed that the cyclosporine powder processed by PDGIMS has no peak at regions characteristic of the existence of crystal forms of the cyclosporine, hence the product must be in amorphous form.

Figure 5:
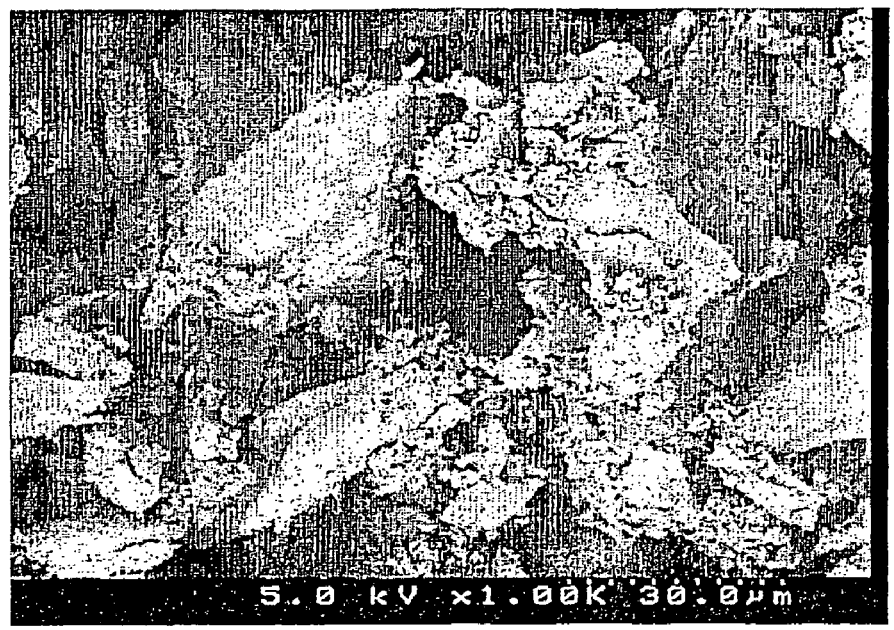
FIG. 5 shows a Scanning Electron Micrograph (SEM) image of a sample of cyclosporine; (a) before processing using the method of the present invention; (b) after being processed using the method of this invention at 25° C. and 160 bar with a 10 mm long, 50 micron diameter nozzle.
Figure 5:
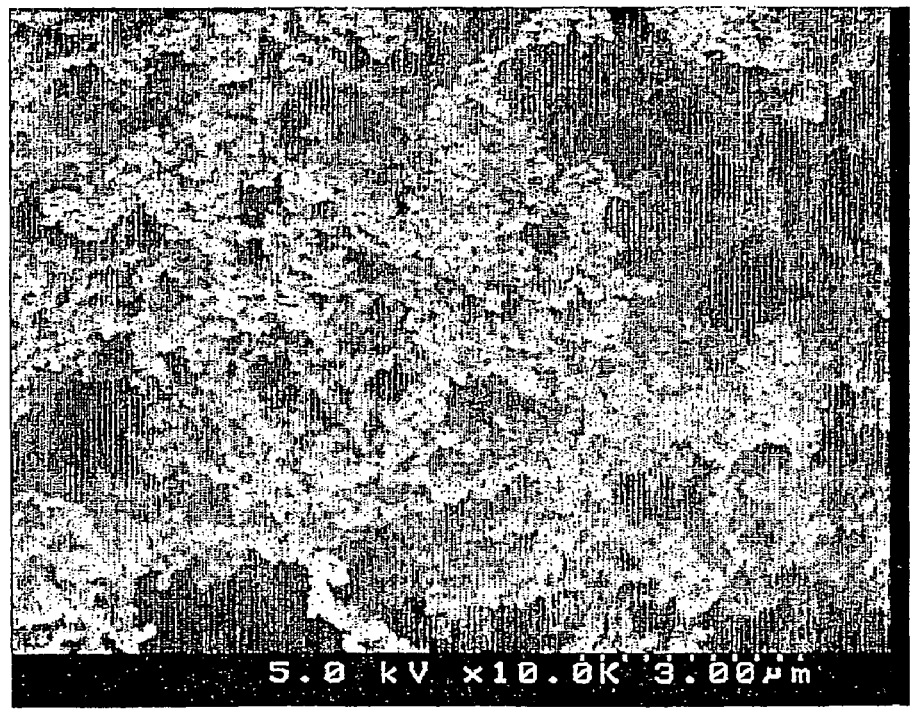
Figure 6:
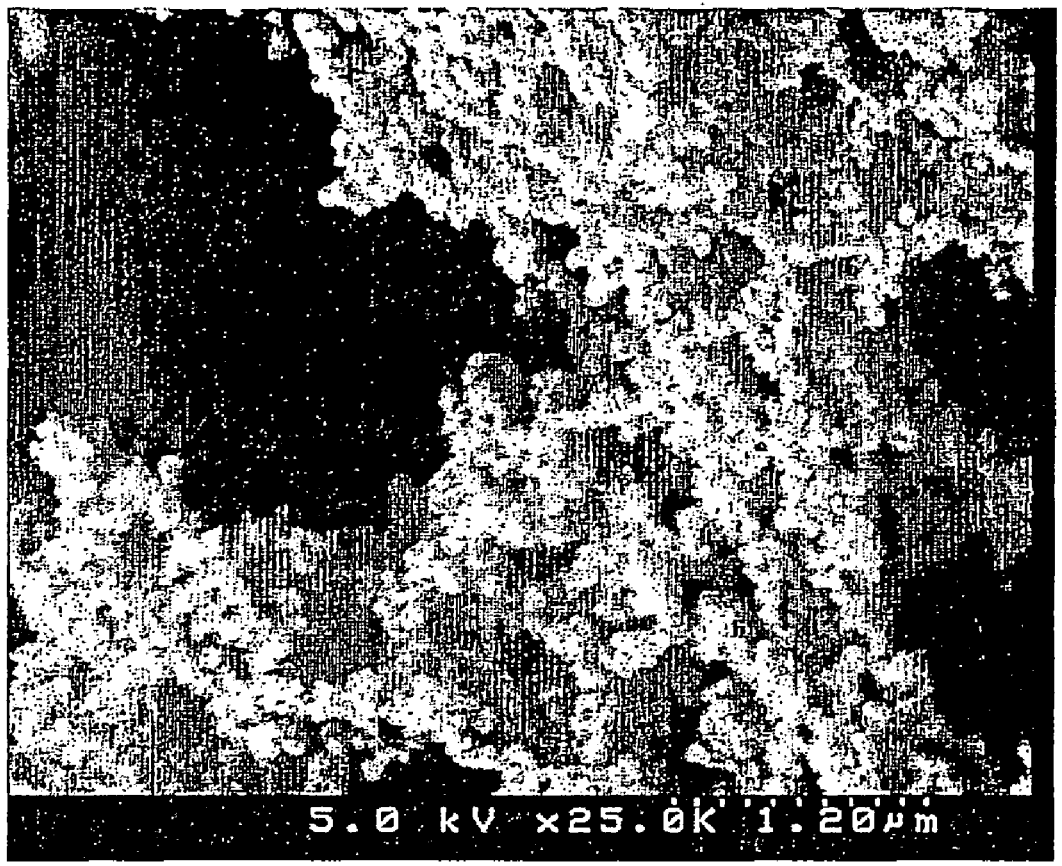
FIG. 6 shows an SEM image of cyclosporine processed according to the method of the invention at 45° C. and 200 bar with a 10 mm long, 50 micron diameter nozzle.
Figure 7:
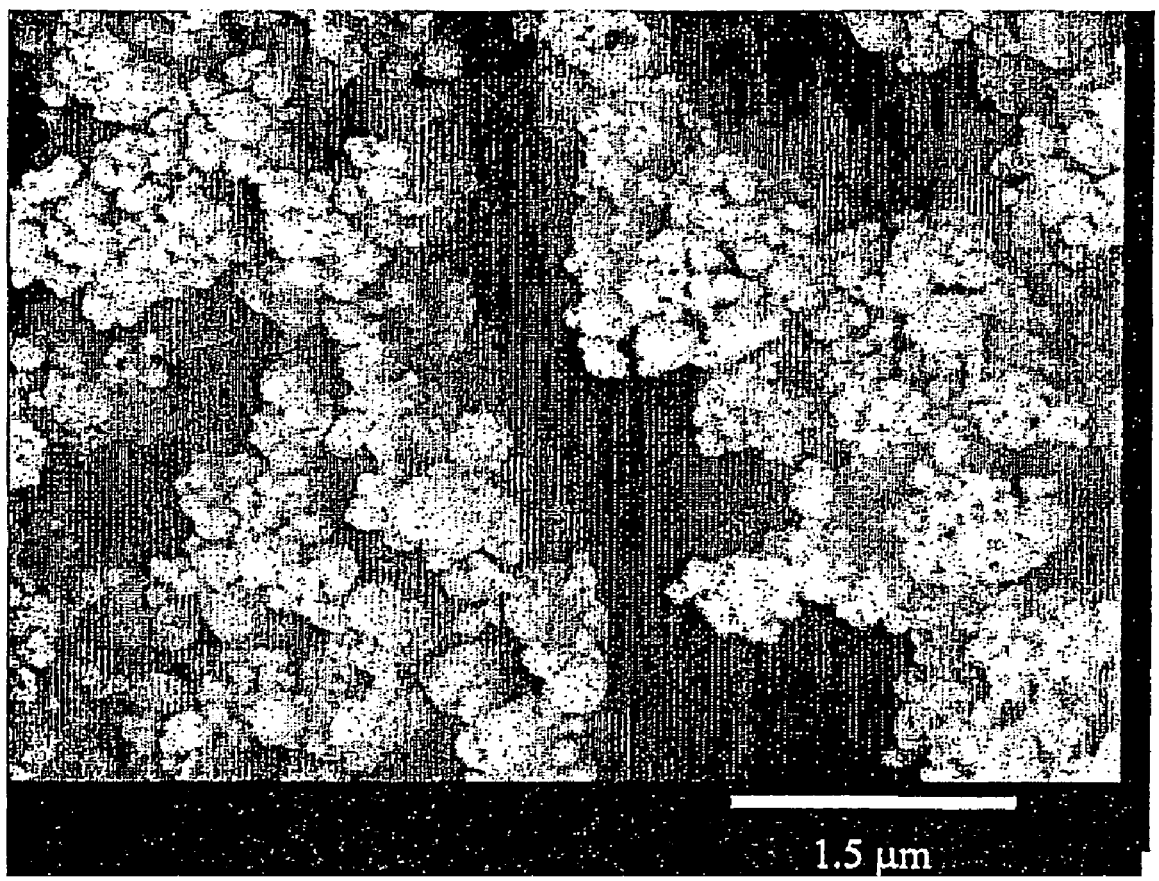
FIG. 7 shows an SEM image of cyclosporine processed at 25° C. and 170 bar.
Figure 9:
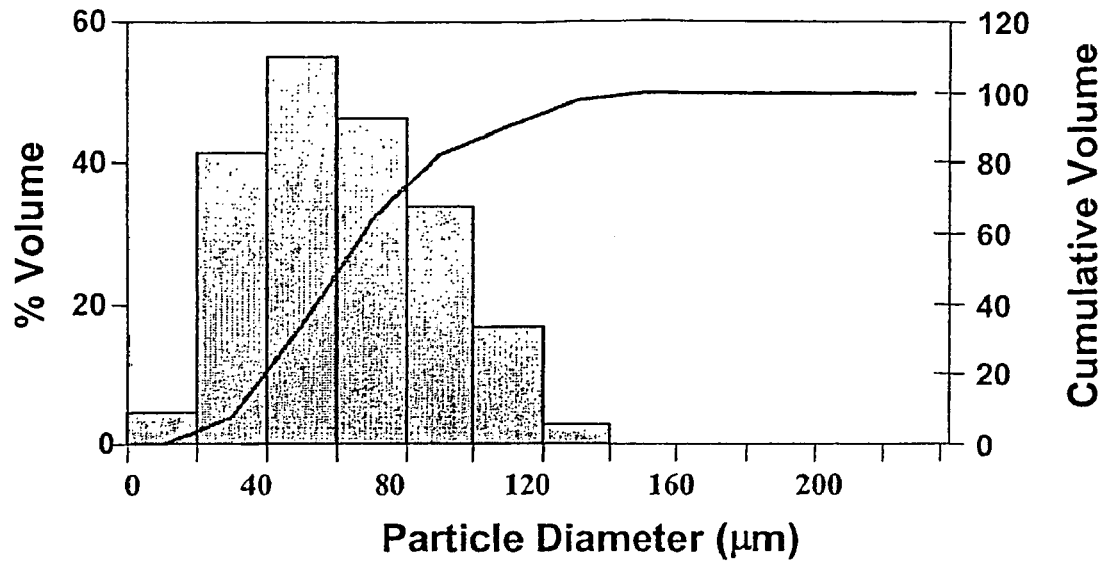
FIG. 9 shows the particle size distribution of cyclosporine, (a) unprocessed powder, (b) processed by PDGIMS.
Figure 9:
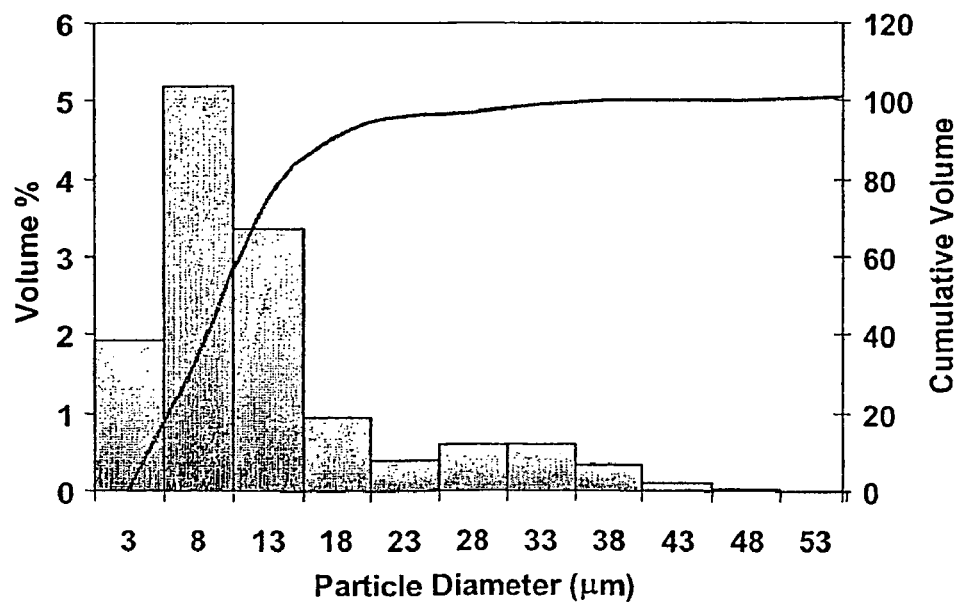

As shown in FIGS. 5, 6 and 7, the primary particles were between 100 and 200 nm in diameter. The particle size distribution of the cyclosporine powder was measured by laser diffraction (Master Size, Malvern Instruments, UK). The primary particles were aggregated in water, however, due to the hydrophobic nature of the cyclosporine, it was not possible to fully disperse the particles. As demonstrated in FIG. 9, which shows the particle size distribution of cyclosporine (a) unprocessed, and (b) processed by PDGIMS, the average particle size and particle size distribution of the cyclosporine processed by PDGIMS was dramatically decreased.

The aerosol performance of the powders for inhalation purposes was characterized by in-vitro testing using a 316 SS Andersen Type Cascade Impactor (COPLEY) equipped with high capacity pump (COPLEY Series HCP3) to generate air flow at the rate of 60 L/min. Approximately 20 mg of the powder was weighed into a gelatin capsule (Size 3, Parke Davis) and inserted into the Aerolizer Inhaler (Novartis) powder inhaler device for dispersion into the cascade impactor. To minimize the bouncing of the powder, the collection plates were coated by methanol-propylene glycol (1:1 volume ratio) and dried for at least 24 hours prior to analysis. The plates were then washed using ethanol and the samples were diluted in a volumetric flask and UV spectroscopy (Hewlett-Packard Vectra-XM Series 3 5/90) at 211 nm was used to determine the mass collected at each stage.

Figure 10:
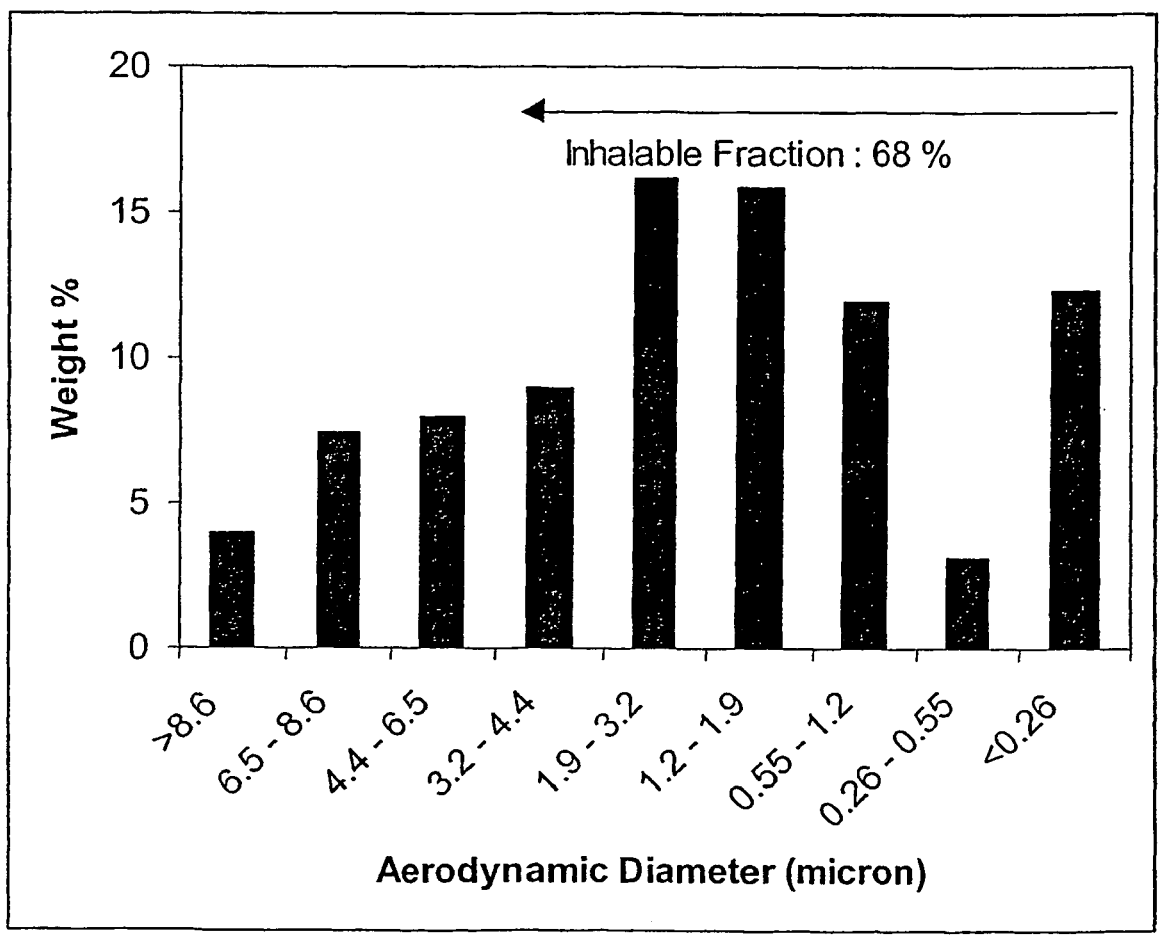
FIG. 10 shows the aerodynamic diameter of cyclosporine produced according to the method of the invention, and measured using a Cascade Impactor.

The results from the cascade impactor for cyclosporine aerosol performance are illustrated in FIG. 10. At a flow rate of 60 L/min flow rate the fine particle mass (<5 μm) of the powder produced from rapid expansion of dense gas solutions was 68%.

The trend that was observed in cyclosporine-$CO_2$ is common for systems where the solid is a heavy and low volatile compound with a critical point far from the critical point of the dense gas.

EXAMPLE 4

Drugs which may be used in combination with cyclosporine include Basiliximab, Tacrolimus, Docetaxel. There is evidence (ref: *J Clin Oncol* 2001 Feb. 15; 19(4): 1160-6) that the bioavailability of docetaxel is strongly enhanced by coadministration of cyclosporine. The invention enables the encapsulation of a compound such as these with cyclosporine.

In an alternative embodiment, cyclosporine may itself be coated, such as by polycaprolactone into nanoparticles. This has been shown to improve the oral bioavailability of cyclosporine and its uptake by lymphocytes, without a corresponding increase in immunosuppression and adverse effects.

Cyclosporine can also be incorporated into lecithin vesicles, as cyclosporine is lipophillic. It is first melted under dense gas and then mixed with a phospholipid, such as lecithin. A surfactant, preferably a non-ionic surfactant (eg, polysorbate, TWEENs, SPANs, polyethoxylated castor oil, etc) may also be added at this point. The mixture is then depressurised into an aqueous solution (rather than into air as in the previous examples). The resulting solution will be an emulsion containing cyclosporine in small vesicles or micelles. This is an efficient way of generating a cyclosporine (or other lipophillic compound) aqueous emulsion, without the cyclosporine decomposing.

Improved bioavailability of cyclosporine has also been shown by forming microspheres containing cyclosporine and sodium lauryl sulphate ("SLS"). In particular, cyclosporine, SLS and dextrin in the ratio of 1:3:1 has been found very effective. The invention can utilise the decreased melting point of cyclosporine in the presence of dense $CO_2$ to create such spheres by then mixing it with the SLS and dextrin in the required ratios.

The invention is equally applicable to cyclosporine derivatives, such as valspodar.

EXAMPLE 5

Fenofibrate is another solid substance which can be manipulated by the method of the invention. Fenofibrate (2-[4-(4-chlorobenzoyl) phenoxy]-2-methyl-propanoic acid, 1-methylethyl ester) has a molecular weight of 361 g/mol and a melting point at atmospheric pressure of 79-82° C. Using the method of the invention, fenofibrate was processed into micron sized particles.

$CO_2$ gas was solubilized in molten fenofibrate and then depressurised rapidly by spraying the solution through a nozzle or orifice as described above, using the apparatus illustrated in FIG. 2. In this configuration, gas is forced from the bottom of the Jerguson Cell to the top. This configuration maintains the gas solution below saturation, thus reducing blockages in the 50 micron nozzle. As a result of the pressure drop, particles were precipitated as a fine powder.

Fenofibrate was processed using the following conditions:
Pre-expansion pressure: 190 bar.
Pre-expansion temperature: 50° C.
Post-expansion pressure: The pressure in the expansion chamber was maintained below 3 bar, with a pressure relief valve.
Post-expansion temperature: The temperature in the expansion chamber was room temperature.
Nozzle size: 50 micron internal diameter.
Particle Collection device: Particles are collected in a Whitey chamber. A low pressure relief valve was used to ensure that the pressure in the collection chamber remained below 3 bar. A 0.5 micron filter was placed at the outlet line of the particle collection device.

The melting point depression of fenofibrate varied as a function of temperature. At and below 35° C., no melting point depression was evident below 200 bar. At 40° C., melting occurred at 88 bar and at 50° C., melting occurred at 68 bar. Therefore at 50° C., the method of the invention is applicable at pressures greater than 68 bar.

Figure 11:
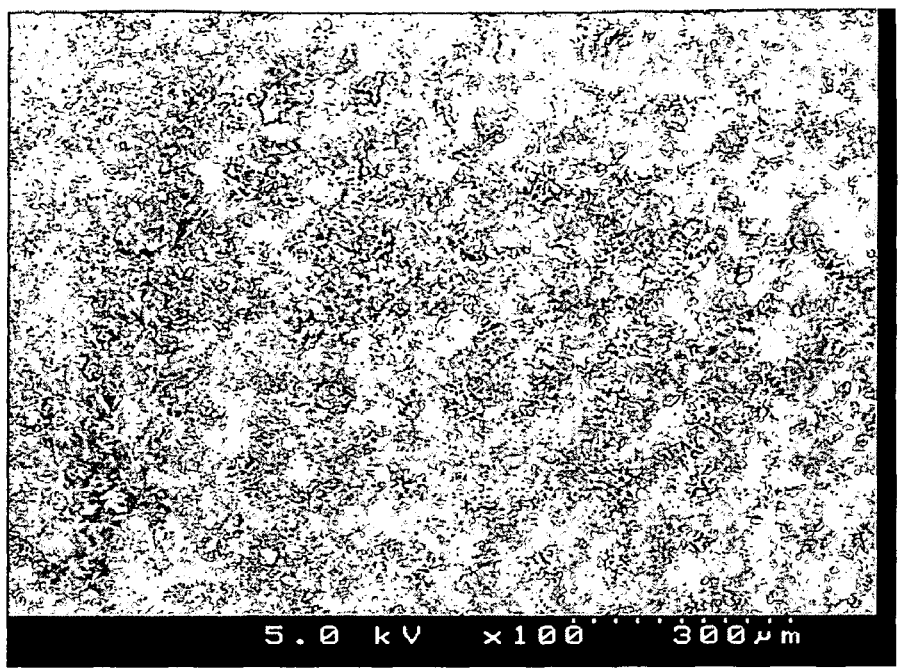
Figure 11:

Unprocessed fenofibrate is provided as large (60 micron) irregular crystals. SEM images at 2 different magnifications, namely 100× (FIG. 11a) and 2510× (FIG. 11b), of fenofibrate processed at 50° C. and 190 are shown in FIG. 11. The particles are not aggregated, and have a particle size of approximately 5-10 microns.

EXAMPLE 6

Gemfibrozil (5-(2,5-dimethylphenoxy)-2,2-dimethylpentanoic acid) is another example of a pharmaceutically active compound which may be a solid substance in the method of the invention, and subjected to dense carbon dioxide. Gemfibrozil has a molecular weight of 250 g/mol and a melting point at atmospheric pressure of 58-61° C. The method of the invention can therefore be used in processing gemfibrozil. Gemfibrozil is very poorly soluble in water and is used as an anti-lipidic drug. Gemfibrozil was used as supplied by Australian Pharmaceutical Ingredients, Sydney, Australia. The material is white in colour.

As before, gemfibrozil was packed in a glass pasteur pipette stoppered with glass wool, and placed in a Jerguson Cell. The Jerguson was thermally equilibrated. Carbon dioxide was introduced to the cell thereby increasing the pressure. The onset of a melting point depression was monitored visually. Again, gas was forced from the bottom of the Jerguson, to the top. At 50° C., a melting point depression was observed at 40 bar.

Figure 12:
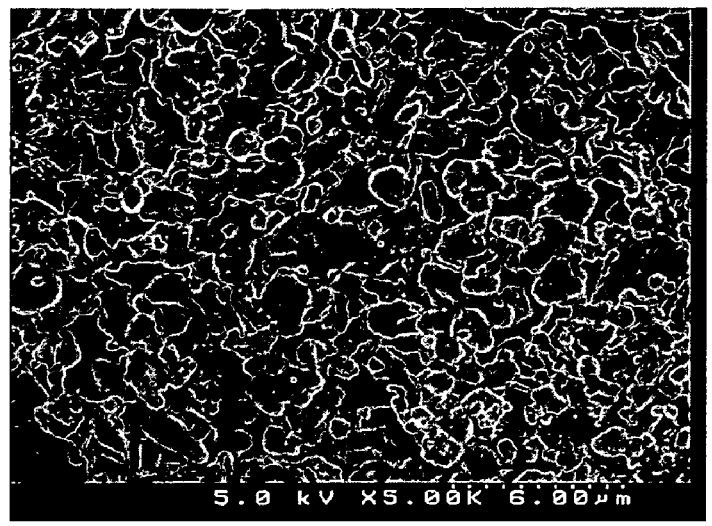
Figure 12:
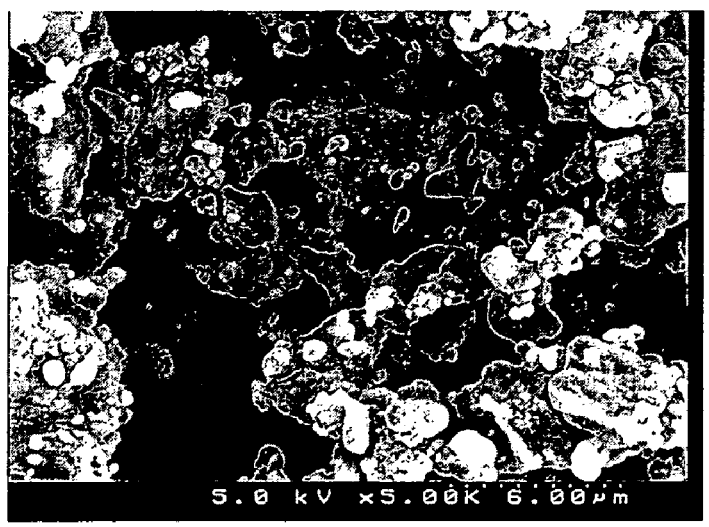

SEM images were taken, using a Hitachi S4500 electron microscope. The samples were chromium coated for 60 seconds with a current of 125 mA, with a Emitech E4500 coater. FIG. 12 contains SEM images of gemfibrozil processed by the method of the invention using $CO_2$ at a pressure of 190 bar and temperatures of 50° C. (image (a)) and 25° C. (image (b)).

The particles formed are approximately 5 microns in size. Particles formed with the dense gas at a sub-critical condition are more polydisperse than those formed at 50° C. At both conditions, around 80 ml of carbon dioxide at 190 bar was used to produce particles, and in both cases around 100 mg of gemfibrozil was produced. The size of the batch was limited by the filter on the outlet of the expansion chamber blocking. The powder was a free flowing fine powder.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for manipulating or formulating a solid substance which melts under pressure of a gas without degrading at a temperature which is lower than the melting point of the substance at atmospheric pressure comprising:
   providing the substance in a pressure chamber having an inlet and an outlet, wherein the outlet is above the inlet;
   applying to the substance a liquefied gas or dense gas to melt the substance without degrading the substance;
   equilibrating the molten substance and the liquefied gas or dense gas to form a homogeneous solution wherein the solution is maintained below saturation; and
   contacting the solution with a carrier fluid, wherein the carrier fluid is passed through the solution and is at substantially the same pressure as the liquefied gas or dense gas, to pass the solution from the pressure chamber through the outlet into a vessel of lower pressure than the pressure of the liquefied gas or dense gas and carrier fluid, and wherein further the solution is maintained below saturation.

2. The method of claim 1, wherein the carrier fluid is the same as the liquefied gas or dense gas.

3. The method of claim 1, further comprising allowing the substance and the liquefied gas or dense gas to equilibrate for at least one minute before the contacting step.

4. The method of claim 3, wherein the equilibration step is for a period of about 2 hours.

5. The method of claim 1, wherein the substance is a pharmaceutical or biological compound.

6. The method of claim 5, wherein the substance is cyclosporine.

7. The method of claim 1, wherein the temperature is between 5° C. and 150° C.

8. The method of claim 1, wherein the pressure of the liquefied gas or dense gas and carrier gas is between 5 bar and 200 bar.

9. The method of claim 8, wherein the liquefied gas or dense gas is carbon dioxide.

10. The method of claim 1, wherein at least 50% of the particles formed are between 50 and 5000 nanometers in diameter.

11. The method of claim 1, wherein over 50% of the particles are less than 5000 nanometers in diameter.

12. The method of claim 1, wherein the particles are encapsulated after the addition of an encapsulating material.

13. The method of claim 12, wherein the encapsulating material is biodegradable.

14. The method of claim 12, wherein the encapsulating material is selected from the group consisting of polyethylene glycol, polyvinylpyrrolidone, poly(d,l-lactide-co-glycolide), poly cellulose acetate.

15. The method of claim 12, wherein the encapsulated particles contain a mixture or combination of the substance and a polymer.

16. The method of claim 5, wherein the substance is gemfibrozil or fenofibrate.

17. The method of claim 1, wherein the solution is passed by the carrier fluid from the pressure chamber through the outlet into a vessel of lower pressure via a pre-pressurized nozzle.

18. A method for manipulating or formulating a solid substance which melts under pressure of a gas without degrading at a temperature which is lower than the melting point of the substance at atmospheric pressure comprising:
   providing the substance in a pressure chamber having an inlet and an outlet, wherein the outlet is above the inlet;
   applying to the substance a liquefied gas or dense gas to melt the substance without degrading the substance;
   equilibrating the molten substance and the liquefied gas or dense gas to form a homogeneous solution wherein the solution is maintained below saturation; and
   contacting the solution with a carrier fluid, wherein the carrier fluid is the same as the liquefied gas or dense gas and is passed through the solution and is at substantially the same pressure as the liquefied gas or dense gas, to pass the solution from the pressure chamber through the outlet into a vessel of lower pressure than the pressure of the liquefied gas or dense gas and carrier fluid, and wherein further the solution is maintained below saturation.

19. A method for manipulating or formulating a solid substance which melts under pressure of a gas without degrading at a temperature which is lower than the melting point of the substance at atmospheric pressure comprising:
   providing the substance in a pressure chamber having an inlet and an outlet, wherein the outlet is above the inlet;
   applying to the substance a liquefied gas or dense gas to melt the substance without degrading the substance;
   equilibrating the molten substance and the liquefied gas or dense gas to form a homogeneous solution wherein the solution is maintained below saturation; and
   contacting the solution with a carrier fluid, wherein the carrier fluid is the same as the liquefied gas or dense gas and is passed through the solution and is at substantially the same pressure as the liquefied gas or dense gas, to pass the solution from the pressure chamber through the outlet into a vessel of lower pressure than the pressure of the liquefied gas or dense gas and carrier fluid, and wherein further the solution is maintained below saturation and the contacting is performed at constant temperature and pressure.

* * * * *